(12) United States Patent
Lec et al.

(10) Patent No.: US 7,857,761 B2
(45) Date of Patent: Dec. 28, 2010

(54) ACOUSTIC BLOOD ANALYZER FOR ASSESSING BLOOD PROPERTIES

(75) Inventors: Ryszard M. Lec, Philadelphia, PA (US);
J. Yasha Kresh, Yardley, PA (US);
David M. Wootton, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 1345 days.

(21) Appl. No.: 10/826,567

(22) Filed: Apr. 16, 2004

(65) Prior Publication Data

US 2005/0015001 A1   Jan. 20, 2005

Related U.S. Application Data

(60) Provisional application No. 60/463,557, filed on Apr. 16, 2003.

(51) Int. Cl.
*A61B 5/00* (2006.01)
(52) U.S. Cl. ...................... 600/368; 600/369
(58) Field of Classification Search .................. 356/40; 600/368–378; 436/69; 73/61.49, 54.24, 73/54.41, 61.45, 61.75, 61.42, 64.49; 422/73
See application file for complete search history.

(56) References Cited

U.S. PATENT DOCUMENTS

| | | | |
|---|---|---|---|
| RE27,703 E | | 7/1973 | Stafford et al. |
| 4,026,671 A | * | 5/1977 | Simons et al. ............... 422/73 |
| 4,149,405 A | * | 4/1979 | Ringrose ................. 73/54.01 |
| 4,430,699 A | | 2/1984 | Segarra et al. |
| 4,484,273 A | | 11/1984 | Stiffler et al. |
| 4,531,193 A | | 7/1985 | Yasuhara et al. |
| 4,558,589 A | * | 12/1985 | Hemmes ................... 73/64.42 |
| 4,591,977 A | | 5/1986 | Nissen et al. |
| 4,599,219 A | | 7/1986 | Cooper et al. ................ 422/61 |
| 4,756,884 A | | 7/1988 | Hillman et al. .............. 422/73 |
| 4,819,149 A | | 4/1989 | Sanik et al. |
| 4,831,558 A | | 5/1989 | Shoup et al. |
| 4,849,340 A | | 7/1989 | Oberhardt .................. 435/13 |
| 4,864,489 A | | 9/1989 | Yasuhara et al. |
| 4,938,068 A | | 7/1990 | Clements |
| 4,969,083 A | | 11/1990 | Gates |
| 4,981,779 A | * | 1/1991 | Wagner ................. 435/287.9 |
| 4,992,926 A | | 2/1991 | Janke et al. |

(Continued)

FOREIGN PATENT DOCUMENTS

AU   2010201142 A1   4/2010

(Continued)

OTHER PUBLICATIONS

Lec, Ryszard M., "Piezoelectric Biosensors:Recent Advances and Applications", IEEE International Frequency Control Symposium and PDA Exhibition 2001 419-429.

(Continued)

*Primary Examiner*—Patricia C Mallari
*Assistant Examiner*—Karen E Toth
(74) *Attorney, Agent, or Firm*—Woodcock Washburn, LLP

(57) ABSTRACT

An acoustic blood analyzer with a transducer section of acoustic biosensors for measurement of blood properties including, but not limited to blood coagulation, platelet function and various blood disorders in a blood sample is provided. Methods for use of the blood analyzer in measurement of blood properties are also provided.

36 Claims, 5 Drawing Sheets

U.S. PATENT DOCUMENTS

| | | | |
|---|---|---|---|
| 5,047,627 A * | 9/1991 | Yim et al. | 250/227.23 |
| 5,048,525 A * | 9/1991 | Maxwell | 600/311 |
| 5,110,727 A | 5/1992 | Oberhardt | 435/13 |
| 5,115,675 A | 5/1992 | Feldman et al. | |
| 5,119,819 A | 6/1992 | Thomas et al. | 128/660.02 |
| 5,122,794 A | 6/1992 | Warrior | |
| 5,131,092 A | 7/1992 | Sackmann et al. | |
| 5,151,978 A | 9/1992 | Bronikowski et al. | |
| 5,159,673 A | 10/1992 | Sackmann et al. | |
| 5,166,678 A | 11/1992 | Warrior | |
| 5,167,145 A | 12/1992 | Butler et al. | 73/64.43 |
| 5,174,291 A * | 12/1992 | Schoonen et al. | 600/322 |
| 5,245,704 A | 9/1993 | Weber et al. | |
| 5,251,302 A | 10/1993 | Weigl et al. | |
| 5,306,644 A * | 4/1994 | Myerholtz et al. | 436/149 |
| 5,329,579 A | 7/1994 | Brunson | |
| 5,333,114 A | 7/1994 | Warrior et al. | |
| 5,372,946 A | 12/1994 | Cusak et al. | 436/69 |
| 5,418,143 A | 5/1995 | Zweig | 435/13 |
| 5,421,328 A * | 6/1995 | Bedingham | 600/309 |
| 5,434,774 A | 7/1995 | Seberger | |
| 5,447,440 A * | 9/1995 | Davis et al. | 435/6 |
| 5,448,231 A | 9/1995 | Takezoe et al. | |
| 5,451,923 A | 9/1995 | Seberger et al. | |
| 5,452,201 A | 9/1995 | Pieronek et al. | |
| 5,453,924 A | 9/1995 | Monson et al. | |
| 5,457,999 A | 10/1995 | Feldman | |
| 5,485,142 A | 1/1996 | Stute et al. | |
| 5,485,400 A | 1/1996 | Warrior et al. | |
| 5,494,639 A * | 2/1996 | Grzegorzewski | 422/82.01 |
| 5,506,956 A | 4/1996 | Cohen | |
| 5,513,324 A | 4/1996 | Dolin, Jr. et al. | |
| 5,537,547 A | 7/1996 | Chan et al. | |
| 5,537,626 A | 7/1996 | Kraslavsky et al. | |
| 5,546,584 A | 8/1996 | Lundin et al. | |
| 5,553,297 A | 9/1996 | Yonezawa et al. | |
| 5,564,419 A * | 10/1996 | Lundsgaard et al. | 600/317 |
| 5,579,482 A | 11/1996 | Einkauf et al. | |
| 5,601,995 A | 2/1997 | Exner | 435/13 |
| 5,608,720 A | 3/1997 | Biegel et al. | |
| 5,682,476 A | 10/1997 | Tapperson et al. | |
| 5,684,451 A | 11/1997 | Seberger et al. | |
| 5,691,896 A | 11/1997 | Zou et al. | |
| 5,706,007 A | 1/1998 | Fragnito et al. | |
| 5,728,583 A * | 3/1998 | Kawakami et al. | 436/69 |
| 5,754,596 A | 5/1998 | Baschoff et al. | |
| 5,764,891 A | 6/1998 | Warrior | |
| 5,764,955 A | 6/1998 | Doolan | |
| 5,768,119 A | 6/1998 | Havekost et al. | |
| 5,793,963 A | 8/1998 | Tapperson et al. | |
| 5,796,602 A | 8/1998 | Wellan et al. | |
| 5,796,721 A | 8/1998 | Gretta, Jr. | |
| 5,801,942 A | 9/1998 | Nixon et al. | |
| 5,805,442 A | 9/1998 | Crater et al. | |
| 5,825,664 A | 10/1998 | Warrior et al. | |
| 5,828,851 A | 10/1998 | Nixon et al. | |
| 5,834,861 A | 11/1998 | Kanzaki et al. | |
| 5,841,654 A | 11/1998 | Verissimo et al. | |
| 5,850,523 A | 12/1998 | Gretta, Jr. | |
| 5,854,890 A | 12/1998 | Ramachandran et al. | |
| 5,859,959 A | 1/1999 | Kimball et al. | |
| 5,862,052 A | 1/1999 | Nixon et al. | |
| 5,881,311 A | 3/1999 | Woods | |
| 5,889,817 A | 3/1999 | Yoshida | |
| 5,903,455 A | 5/1999 | Sharpe, Jr. et al. | |
| 5,909,368 A | 6/1999 | Nixon et al. | |
| RE36,263 E | 8/1999 | Janke et al. | |
| 5,952,560 A * | 9/1999 | Collings et al. | 73/61.75 |
| 5,960,214 A | 9/1999 | Sharpe, Jr. et al. | |
| 5,963,147 A | 10/1999 | Westfield et al. | |
| 5,970,430 A | 10/1999 | Burns et al. | |
| 5,975,737 A | 11/1999 | Crater et al. | |
| 5,978,578 A | 11/1999 | Azarya et al. | |
| 5,978,850 A | 11/1999 | Ramachandran et al. | |
| 5,980,078 A | 11/1999 | Krivoshein et al. | |
| 5,982,362 A | 11/1999 | Crater et al. | |
| 5,995,916 A | 11/1999 | Nixon et al. | |
| 6,014,612 A | 1/2000 | Larson et al. | |
| 6,017,143 A | 1/2000 | Eryurek et al. | |
| 6,026,352 A | 2/2000 | Burns et al. | |
| 6,032,208 A | 2/2000 | Nixon et al. | |
| 6,044,305 A | 3/2000 | Larson et al. | |
| 6,046,051 A * | 4/2000 | Jina | 436/69 |
| 6,047,220 A | 4/2000 | Eryurek | |
| 6,047,222 A | 4/2000 | Burns et al. | |
| 6,061,603 A | 5/2000 | Papadopoulos et al. | |
| 6,078,320 A | 6/2000 | Dove et al. | |
| 6,094,600 A | 7/2000 | Sharpe, Jr. et al. | |
| 6,095,674 A | 8/2000 | Verissimo et al. | |
| 6,098,116 A | 8/2000 | Nixon et al. | |
| 6,119,047 A | 9/2000 | Eryurek et al. | |
| 6,151,625 A | 11/2000 | Swales et al. | |
| 6,200,532 B1 | 3/2001 | Wu et al. | 422/73 |
| 6,311,549 B1 * | 11/2001 | Thundat et al. | 73/54.24 |
| 6,338,821 B1 * | 1/2002 | Jina | 422/73 |
| 6,508,104 B1 * | 1/2003 | Deluca et al. | 73/53.01 |
| 6,524,861 B1 * | 2/2003 | Anderson | 436/69 |
| 6,543,274 B1 * | 4/2003 | Herrmann et al. | 73/32 A |
| 6,673,622 B1 * | 1/2004 | Jina | 436/69 |
| 6,709,390 B1 * | 3/2004 | Marie Pop | 600/368 |
| 7,223,365 B2 * | 5/2007 | Freiherr Von Der Goltz | 422/68.1 |
| 7,310,543 B2 * | 12/2007 | Smart et al. | 600/345 |
| 2001/0003804 A1 | 6/2001 | Papadopoulos et al. | |
| 2001/0044584 A1 * | 11/2001 | Kensey | 600/504 |
| 2002/0007665 A1 * | 1/2002 | Miura | 73/54.25 |
| 2002/0124634 A1 * | 9/2002 | Litton | 73/54.25 |
| 2002/0169394 A1 * | 11/2002 | Eppstein et al. | 600/573 |
| 2003/0212347 A1 * | 11/2003 | Sohrab | 600/584 |
| 2004/0054283 A1 * | 3/2004 | Corey et al. | 600/438 |
| 2004/0072357 A1 * | 4/2004 | Stiene et al. | 436/69 |
| 2004/0157337 A1 * | 8/2004 | Burke et al. | 436/70 |
| 2004/0214337 A1 * | 10/2004 | Kautzky | 436/70 |
| 2004/0216515 A1 * | 11/2004 | Yakhno et al. | 73/64.53 |
| 2004/0249292 A1 * | 12/2004 | Davis et al. | 600/481 |
| 2005/0148899 A1 * | 7/2005 | Walker et al. | 600/553 |
| 2005/0212869 A1 * | 9/2005 | Ellson et al. | 347/75 |
| 2005/0233466 A1 * | 10/2005 | Wright et al. | 436/165 |
| 2006/0079740 A1 * | 4/2006 | Silver et al. | 600/309 |

FOREIGN PATENT DOCUMENTS

| | | |
|---|---|---|
| WO | WO 98/02993 | 1/1998 |
| WO | WO 99/48245 | 9/1999 |

OTHER PUBLICATIONS

Lee et al., "Acoustic Wave Biosensors", Proceedings of the 20th Annual International Conference of the IEEE Engineering in Medicine and Biology Society 1998 20(6):2779-2784.

Arpaia et al., "A Distributed Laboratory Based on Object-Oriented Measurement Systems", Measurement, vol. 19, No. ¾, pp. 207-215, 1996.

Cheah et al., "Design and Implementation of an MMS Environment on Isode", Computer Communications, vol. 20, pp. 1354-1364, 1997.

Drakopoulos, Elias, "Enterprise Network Planning and Design: Methodology and Application", Computer Communications, vol. 22, pp. 340-352, 1999.

File History: Crater et al., "Distributed Interface Architecture for Programmable Industrial Control Systems", U.S. Patent No. 5,805,442, Issued Sep. 8, 1998, U.S. Appl. No. 08/655,469, filed May 30, 1996.

File History: Crater et al., "Distributed Interface Architecture for Programmable Industrial Control Systems", U.S. Patent No. 5,975,737, Issued Nov. 2, 1999, U.S. Appl. No. 09/112,583, filed Jul. 9, 1998.

File History: Janke et al., Peer-to-Peer Register Exchange Controller for Industrial Programmable Controllers, U.S. Patent No. 4,992,926, Issued Feb. 12, 1991, U.S. Appl. No. 07/258,779, filed Oct. 17, 1988.

He et al., "Clock Synchronization in Real-Time Distributed Systems Based on FIP Field Bus", Centre de Recherche en Informatique de Nancy, pp. 135-141, Sep. 30, 1990.

Lonn et al., "Synchronisation in Safety-Critical Distributed Control Systems", Chalmers University of Technology, Laboratory for Dependable Computing, pp. 891-899, Apr. 19, 1995.

Middeldorp et al., "DFS 2929 Foreign Device Interfaces", pp. 1-13, Oct. 2, 1987.

Middeldorp et al., "CPS 1259 Foreign Device Interface", pp. 1-11, Nov. 3, 1987.

Olson et al., "Probabilistic Clock Synchronization in Large Distributed Systems", Real-Time Computing Laboratory, pp. 290-297, May 20, 1991.

Shaughnessy, Ed, "DFS 1592 Master Timekeeper", pp. 1-32, Mar. 19, 1986.

Andersson L. I., "Molecular imprinting:developments and applications in the analytical chemistry field", Journal of Chromatography B 2000 745:3-13.

Carville et al., "Coagulation testing—Part 1:Current methods and challenges", IVD Technology Magazine 1998 4(4):59-66.

Fuster et al., "Optimal Therapeutic Ranges for Oral Anticoagulation", Saunders 1992 161-173.

Geerts et al., "Thromboembolism in Trauma:The Problem and Its Prevention", Seminars in Thrombosis and Hemostasis 1996 22(2):19-24.

Gravlee et al., "Predictive Value of Blood Clotting Tests in Cardiac Surgical Patients", Ann Thoracic Surg 1994 58:216-221.

Hirsh et al., "Treatment of Venous Thromboembolism", Hemostasis and Thrombosis:Basic Principles and Clinical Practice 1994 Chapter 69 1346-1366.

Josse et al., "On the mass sensitivity of acoustic-plate-mode sensors", Sensors and Actuators 1996 A(53):243-248.

Kane et al., "Patterning proteins and cells using soft lithography", Biomaterials 1999 20:2363-2376.

Lal A., "Silicon-Based Ultrasonic Surgical Actuators", Proceedings of the 20th Annual International Conference of the IEEE Engineering in Medicine and Biology Society 1998 20(6):2785-2790.

Levine et al., "Hemorrhagic Complications of Long-Term Antithrombotic Treatment", Thrombosis in Cardiovascular Disorders 1992 515-522.

Narins et al., "Relation Between Activated Clotting Time During Angioplasty and Abrupt Closure", Circulation 1996 93:667-671.

Ogilby et al., "Adequate Heparinization During PTCA:Assessment Using Activated Clotting Times", Catheterization and Cardiovascular Diagnosis 1989 18:206-209.

Shore-Lesserson et al., "Thromboelastography-Guided Transfusion Algorithm Reduces Transfusions in Complex Cardiac Surgery", Anesth Analg 1999 88:312-319.

Zeynep Mörel: "Platelet Adhesion to Various Surfaces Studied by On-Line Acoustic Wave sensor" M.SC. Thesis, University of Toronto, [Online] 1999, XP002511376 Ottawa ISBN: 0-612-45517-3 Retrieved from the Internet: URL:http://www.collectionscanada.gc.ca/obj/s4/f2/dsk1/tape7/PQDD_0007/MQ45517.pdf> [retrieved on Jan. 21, 2009].

Sorial, Joseph: "A Piezoelectric Interfacial Phenomena Biosensor" A Thesis Submitted to the Faculty of Drexel University by Joseph Sorial in Partial Fulfillment of the Requirements for the Degree of Masters of Science, [Online] Dec. 2000, XP002511377 Drexel University Retrieved from the Internet: URL:http://dspace.

Valdeiglesias, J.R.P., Machado, J.C.: "Platelet aggregation detected by ultrasound" Engineering in Medicine and Biology Society, Proceedings of the Annual International Conference of the IEEE, ISBN: 0-7803-0216-8, vol. 13, No. 1, 1991, pp. 154-155, XP002511378.

Voleisis A et al: "Ultrasonic method for the whole blood coagulation analysis" Ultrasonics, IPC Science and Technology Press Ltd. Guildford, GB, vol. 40, No. 1-8, May 1, 2002, pp. 101-107, XP004357178 ISSN: 0041-624X.

Alves C H F et al: "Measurement of plasma clotting time using ultrasonic shear waves" Physiological Measurement, Institute of Physics Publishing, Bristol, GB, vol. 15, No. 3, Aug. 1, 1994, pp. 309-316, XP020073988 ISSN: 0967-3334.

Shyh-Hau Wang et al: "Detection of the process of blood coagulation and clot formation using quantitative ultrasonic parameters" 2002 IEEE Ultrasonics Symposium. Proceedings (Cat. No. 02CH37388) IEEE Piscataway, NJ, USA, vol. 2, 2002, pp. 1653-1656 vol. XP002511379 ISBN: 0-7803-7582-3.

AU Examination Report, Australian Government IP Australia, Jun. 25, 2009, 2 pages.

EPC Examination Report, European Patent Office, Dec. 4, 2009, 5 pages.

International Preliminary Report on Patentability, Chapter 1, PCT/US2004/011845, Jan. 23, 2007, 4 pages.

International Search Report, PCT/ US2004/011845, of WO2004/093641 A3, May 10, 2007, 2 pages.

Kazys et al., "Ultrasonic method for the whole blood coagulation analysis," no month available, 2002, 101-107.

Written Opinion of the International Searching Authority, PCT/US2004/011845, Jan. 19, 2007, 3 pages.

* cited by examiner

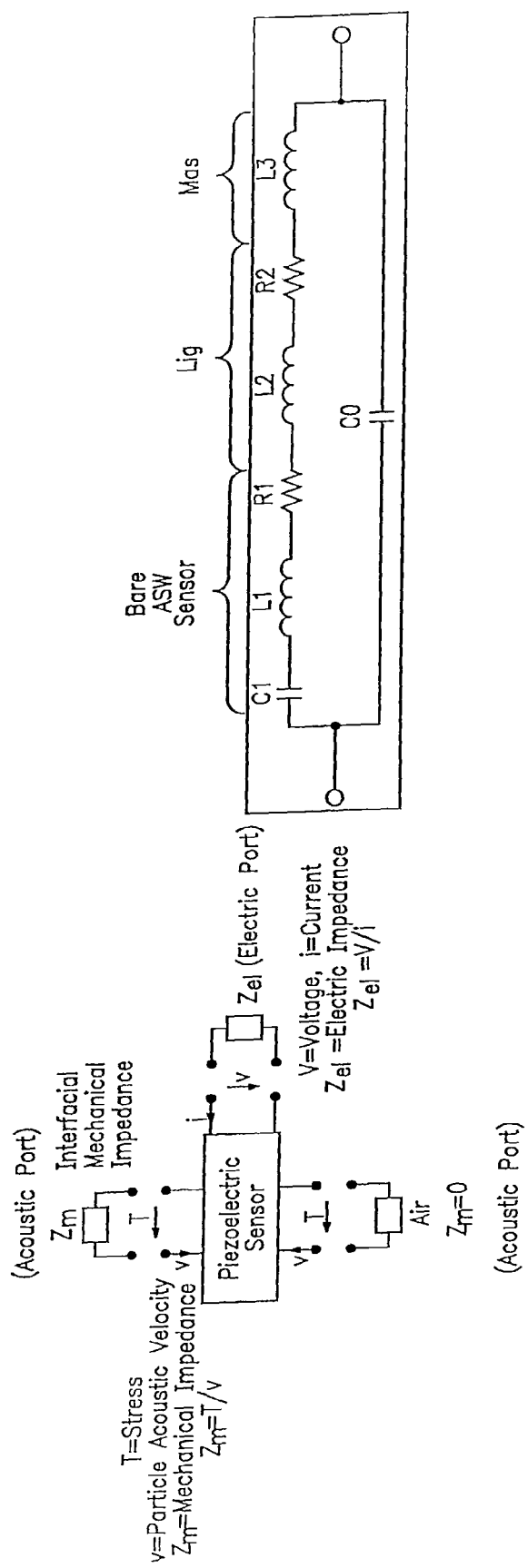

ACOUSTIC BLOOD ANALYZER FOR ASSESSING BLOOD PROPERTIES

This application claims the benefit of priority from U.S. Provisional Application Ser. No. 60/463,557, filed Apr. 16, 2003, which is herein incorporated by reference in its entirety.

FIELD OF THE INVENTION

An acousto-mechanical blood analyzer, also referred to herein as an acoustic blood analyzer, is provided with a point-of-care and self-test clotting sensor that measures multiple blood properties including, but not limited to, blood coagulation and platelet function. The acousto-mechanical blood analyzer comprises a transducer section of one or more acoustic sensors. Preferably the acoustic sensor or sensors further comprises a bioactive surface or coating which promotes specific blood-sensor interactions. The analyzer also preferably further comprises a blood sampling means, a fluidic section to deliver and distribute a blood sample to the acoustic sensor or sensors, an electronic section means, which excites the acoustic sensor or sensors and detects changes in the operational parameters of the transducer section, and a packaging section or housing which provides mechanical and functional integrity to the transducer, fluidic, and electronic section means of the analyzer. This packaging section also provides an interface for the analyzer with analytical laboratory systems and computer based data processing, storage and display systems. Methods for using the acoustic blood analyzer to measure blood properties including, but not limited to, blood coagulation and platelet function are also provided. The analyzer and methods of the present invention are particularly useful in identifying, diagnosing, and monitoring subjects at high risk for blood clots and excessive bleeding.

BACKGROUND OF THE INVENTION

Thrombotic disease is considered to be a major health problem affecting millions of patients in the United States alone and its manifestations cause significant morbidity and mortality. Estimates of incidence vary because many of the events go unnoticed, including the fatal ones. In particular, as many as 2,000,000 Americans each year suffer from deep vein thrombosis (clots) in one form or another. Approximately half of these incidences occur in surgical patients or individuals with cancer, other illnesses or trauma while the other half occurs for no known reasons. Surgical procedures in general predispose patients to risk of developing blood clots that may result in life-threatening clinical conditions, including deep vein thrombosis (DVT), pulmonary embolism (PE) or stroke. Procedures in which such risks are especially high include cardio-pulmonary bypass surgery (CPB), coronary artery bypass grafting (CABG), gynecological procedures, neurosurgery, orthopedic surgery, percutaneous transluminal coronary angioplasty (PTCA), and posttrauma reconstructive surgery (Geerts, W. H. Semin Thromb. Hemost. 1996 22(2):19-24; Poller, L. and Hirsh, J. "Optimal Therapeutic Ranges for Oral Anticoagulation," in *Thrombosis in Cardiovascular Disorders*, Fuster V, Verstraete M (eds), Philadelphia, Saunders, pp 161-173, 1992; Ogilby et al. Cath Cardio Diag, 1989 18:206-209; Narins et al. Circulation, 1996 93:667-671). The risk of clotting is relatively high for these operations because they are inherently more invasive and expose the patient's blood to foreign surfaces that can initiate coagulation. To minimize the risks associated with such surgical procedures, patients are placed on anticoagulants (blood thinners). Without appropriate prophylaxis, it is estimated that thrombotic complications would occur in as many as 50% of patients undergoing orthopedic surgery and as many as 25% of patients undergoing other surgeries.

Individuals at particularly high risk for developing blood clots are those who have had them in the past. Clots form most commonly in the legs, but many (>50%) travel to the lungs, resulting in pulmonary embolism (which can be fatal).

New antithrombins and antiplatelet agents are now available to better manage these complex conditions and more efficiently control the thrombotic process. A new generation of oral anticoagulants is also being used extensively in outpatient settings. In the United States, more than 1.5 million people with atrial fibrillation or mechanical heart valves are currently taking some kind of oral anticoagulant to help prevent stroke. A resulting complication of these treatments, however, is often bleeding, which can be severe. As a result, patient monitoring is critical to ensure appropriate treatment regimens. To ensure that surgical patients receive the correct dose of anticoagulant and antithrombotic agents, each patient's hemostatic status/ranking before, during, and after the surgical procedure must be assessed. Importantly, for patients who are placed on long-term oral anticoagulant therapy, additional postdischarge monitoring is of particular value (Hirsh J, Salzman E W, Marder V J, "Treatment of Thromboembolism," in *Hemostasis and Thrombosis: Basic Principles and Clinical Practices* (3rd ed), Colman R C, Hirsh J, Marder V J, et al. (eds), Philadelphia, Lippincott, pp 1346-1366, 1994). The traditional coagulation tests have been available for decades. The majority of such tests are functional end-point assays, in which a patient sample (plasma or whole blood) is incubated with exogenous reagents that activate the coagulation cascade, and the time to clot formation is measured. The clotting time of the patient sample is then compared to the clotting time of pooled normal plasma or whole blood to provide a standard measurement of the patient's hemostatic status. These clotting assays are commonly used as screening tests that evaluate the functioning of both the patient's intrinsic and extrinsic coagulation systems (Carville, D. G. M. and Guyer, K. E. IVD Tech 1998 4(4):59-66).

The Activated Partial Thromboplastin Time Test (APTT) is used to evaluate the intrinsic coagulation pathway, which includes factors I, II, V, VIII, IX, X, XI, and XII. The test is performed using a plasma sample, in which the intrinsic pathway is activated by the addition of phospholipid, an activator (ellagic acid, kaolin, or micronized silica), and $Ca^{2+}$. Formation of the Xase and prothrombinase complexes on the surface of the phospholipid enables prothrombin to be converted into thrombin, with subsequent clot formation. The result of the APTT test is the time (in seconds) required for this reaction. APTT is used to assess the overall competence of a patient's coagulation system, as a preoperative screening test for bleeding tendencies, and as a routine test for monitoring heparin therapy.

The Activated Clotting Time Test (ACT) is a screening test that resembles the activated partial thromboplastin time (APTT) test, but is performed using fresh whole blood samples. ACT is used primarily to monitor a patient's coagulation status in connection with "invasive" procedures that involve the administration of high doses of heparin (e.g., CPB and PTCA). It is important to monitor a patient's response to heparin during such procedures because under dosing can result in pathological thrombus formation, whereas overdosing can lead to serious hemorrhagic complications.

The Prothrombin Time Test (PT) was first described in the mid 1930s. The PT test measures the tissue factor-induced coagulation time of blood or plasma. It is used as a screening test to evaluate the integrity of the extrinsic coagulation pathway, and is sensitive to coagulation factors I, II, V, VII, and X. The test is performed by adding thromboplastin and $Ca^{2+}$ to a patient sample and measuring the time for clot formation. A prolonged clotting time suggests the presence of an inhibitor to, or a deficiency in, one or more of the coagulation factors of the extrinsic pathway. But PT clotting time can also be prolonged for patients on warfarin therapy, or for those with vitamin K deficiency or liver dysfunction. The PT test can provide an assessment of the extrinsic coagulation pathway, and is widely used to monitor oral anticoagulation therapy.

The Thrombin Clotting Time Test (TCT) measures the rate of a patient's clot formation compared to that of a normal plasma control. The test is performed by adding a standard amount of thrombin to a patient's plasma that has been depleted of platelets, and measuring the time required for a clot to form. This test has been used as an aid in the diagnosis of disseminated intravascular coagulation (DIC) and liver disease.

These traditional coagulation tests are all generally performed in a central laboratory, and not in near-patient settings or by self-testing.

Beyond the commonly used test for screening, there are a number of more complex tests that may be used in the diagnosis of a patient's coagulative status. The assays enable clinicians to reduce the number of possible explanations for a prolonged clotting time found in screening assays such as APTT, PT, and TCT.

One such test is a clotting assay for factor VIIa, which has found utility in monitoring patients with severe factor IX deficiency. The level of factor VIIa in these patients has been reported to be less than 10% of the level found in healthy control subjects.

An assay for factor VIII is useful as a diagnostic test for classical hemophilia.

An assay is also available for measuring the level of the activation peptide factor IXa or the factor IXa-antithrombin III complex. These measurements are used to determine the levels of factor IXa or factor VII-tissue mediated complex. Patients with congenital deficiencies of factor VII may be monitored with this test.

Assays for activated protein C resistance, antithrombin, protein C deficiency, and protein S deficiency are also available. Asymptomatic individuals who have heterogeneous deficiencies of proteins C and S, and resistance to activated protein C, have significantly elevated levels of the prothrombin fragment F1.2 compared to controls. More recently, immunochemical assays have been developed that characterize a patient's hemostatic status by determining the concentration of peptides, proteins, and factors of the coagulation cascade found in the patient's sample.

In addition to the factors of the coagulation cascade, platelets play an extremely important role in hemostasis. There is a growing number of antiplatelet agents that are indicated for use in conjunction with anticoagulants. Some of the more common antiplatelet agents include aspirin (a weak antiplatelet agent that affects cyclooxygenase activity during the life of the platelet), clopidogrel and ticlopidine (inhibitors of ADP-mediated activation), and various glycoprotein IIb/IIIa (GPIIb/IIIa) antagonists.

These agents are now recognized as having an extremely important role in the prevention of thromboembolic processes, and the most effective medicines, the GPIIb/IIIa inhibitors, require careful dosing and monitoring to avoid the adverse side effect of hemorrhagic (bleeding) complications.

Thus, monitoring of antiplatelet therapy is also of major interest in most clinical settings where invasive procedures are performed.

In addition to clotting time assays which measure the dynamics of various parts of the coagulation cascade, several assays of the physical properties of the clot, which indicate the combined effects of platelets, fibrin, in concert the coagulation cascade, are available and often used to manage patients in cardiovascular surgery and other critical arenas. The TEG® Coagulation Analyzer monitors the thrombodynamic properties of blood as it is induced to clot under a low shear environment resembling sluggish venous flow. The patterns of changes in shear elasticity enable the determination of the kinetics of clot formation and growth as well as the strength and stability of the formed clot. The strength and stability of the clot provide information about the ability of the clot to perform the work of hemostasis, while the kinetics determine the adequacy of qualitative factors available to clot formation. Other physical clotting assays such as the clot rheometer and the sonoclot analyzer have been developed. At this time, physical clotting assays indicate some platelet-related hemostatic deficiencies, but cannot directly assay platelet aggregation or adhesion.

For the majority of patients, laboratory monitoring may not be feasible for a variety of practical reasons. Consequently, near-patient ("self-test") hemostasis testing technologies have to provide rapid results in both the clinical and in the outpatient settings. These technologies when fully developed will make significant impact on the choice of therapeutic interventions, patient follow-up and management strategy.

Advances made in microfabrication technologies, inexpensive signal processing systems, and the progress in design of biological sensing interfaces have made possible the development of a variety of new biosensors. One of the emerging applications in the delivery of health care is what is becoming known as near-patient or personalized medicine. For example, there is an increasing use of personal monitoring devices such as glucose sensors for diabetics and for HIV detection.

Near-patient (self administered) tests using novel analyzers that boast microvolume test capabilities for blood coagulation have been described. Such tests have been promoted for use in both acute areas of the hospital and by outpatients (e.g., on warfarin therapy) who do not have easy access to a central coagulation laboratory. Patients must be specifically trained, however, to perform the currently available prothrombin time (PT) self-testing at home. Accordingly, the suitability and accuracy of such advanced technologies for assessing the adequacy of a patient's hemostatic system remains a concerns because of the potential for active surface-to-volume effects when small samples are employed, the complexity of the medium being tested (i.e., blood), and the effects that sample processing can have on both the coagulation and thrombotic pathways.

A number of patents describe coagulation measurement using a variety of methods and devices.

For example, U.S. Pat. Nos. 5,110,727 and 4,849,340, disclose a commercial point-of-care system referred to as TAS (Thrombolytic Assessment System). The TAS system uses paramagnetic iron oxide particles (PIOP)/dry chemistry technology. It is based on near-infrared sensing of the motion of PIOP contained in a dry reagent situated as a film on the surface of a flat-capillary reaction chamber mounted on a plastic test card. The PIOP are subjected to an oscillating magnetic field generated by the instrument in which the test card is placed. When blood or plasma is added to a sample well of the test card, the sample enters the reaction chamber, reconstituting the reagent and freeing the PIOP so that they can move in response to changes in the magnetic field with time. The PIOP motion changes when an in vitro thrombus forms. This change results from PIOP entrapment during fibrin polymerization or release during fibrinolysis, providing a kinetic response curve from which the analyzer determines clotting time and a parameter characterizing fibrinolysis process. The TAS system is used commercially in several products.

U.S. Pat. No. 3,695,842 describes a precision magnet in a reagent-containing test tube for measurement of clot formation. When the test tube is filled with sample and inserted in a test well containing a magnetic detector, the tube slowly rotates. When the clot begins to form, a change in the position of the magnet is detected.

U.S. Pat. No. 5,372,946 discloses a disposable cuvette within which is formed a capillary conduit having at least one restricted region for measurement of clot formation. In this device, blood is forced to flow through the restricted region back and forth within a test channel. Two photo-optical detectors are used to measure the speed of sample movement. This patent sets forth the basis for the ProTime microcoagulation system.

U.S. Pat. No. 4,756,884 discloses a technology developed by Biotrack based on optical measurement of a speckle pattern from cells or particles from a sample illuminated by coherent light and flowing in a long capillary track of a plastic reagent-containing cartridge. When clotting occurs, the speckle pattern measurement indicates cessation of flow in the capillary track.

U.S. Pat. No. 4,599,219 discloses a cylindrical plastic cartridge with a plunger assembly terminating in a "flag" at one end and a "daisy" at the other end. The plunger, situated in a reaction chamber above a reagent chamber, is moved by an external mechanical actuator. Flag movement through the clot reaction chamber is timed by a photo-optical detector, the end point being established when fibrin forms on the daisy and slows the plunger movement. This patent sets forth the basis for the Medtronic ACT-II and HepconHMS coagulation assays.

U.S. Pat. No. 5,167,145 describes a technology for measuring clot formation, which uses infrared electromagnetic energy. Infrared electromagnetic transmission changes through a sample from a source of infrared energy to suitable detection electronics producing a peak signal representing the clotting time.

U.S. Pat. No. 5,601,995 discloses a method where a blood sample is applied to a porous sheet and at least one of a spreading extent and a spreading rate are measured by either an optical property, or an electrical potential across the porous sheet to determine the propensity of the sample to coagulate.

U.S. Pat. No. 5,418,143 discloses a method for detecting clot formation in a whole blood sample using a test strip comprising a porous membrane having a coagulation initiator and a substrate impregnated therein. The substrate is activated by thrombin, and produces a detectable fluorescent signal as the output.

U.S. Pat. No. 6,200,532 discloses several technologies applied to point-of-care blood clot measurement, based on motion of a magnetically excited "bender" which deforms the blood sample. The bender motion is detected by piezoelectric or optical means. This patent also describes sample handling, reagent mixing, packaging, and the use of microporous membranes to separate plasma from blood cells for conducting plasma assays. Use of a piezoelectric transducer to measure changes to an electromagnetic wave in the coagulating blood sample is also described.

However, these above-described methods and devices have disadvantages in their complexity resulting from the use of two or more distinct mechanisms to probe or perturb the clotting blood, and to measure the response of the clot. Further, they lack specificity, in that they can only measure coagulation or platelet aggregation in bulk and/or in response to bulk stimulants. In addition, many of these devices do not differentiate between clots of differing mechanical properties, and those methods that do (e.g. TEG) are expensive, cumbersome and require specialized training and large blood sample volumes.

Thus, there is a need for better near-patient/self-test assays capable of accurate and timely platelet-function testing as well as analysis of the coagulation status of blood. The optimal near-patient/self test coagulation analyzer will be of small size and light weight for portability, capable of achieving physiological temperatures (37° C.), and easy to use and requiring no specialized training. This analyzer is preferably capable of producing rapid quantitative results to local as well as remote sites using reagents that have been standardized to provide international normalized ratios. The analyzer must require only small sample sizes of whole blood. Preferably, components of the analyzer contacting the patient sample are disposable and the entire equipment and operating costs for the analyzer are relatively low.

SUMMARY OF THE INVENTION

An object of the present invention is to provide an acoustic blood analyzer with a point-of-care and self-test clotting sensor that measures blood properties including, but in no way limited to, coagulation and platelet function. In simplest form, the acoustic blood analyzer comprises a transducer section of one or more acoustic sensors, preferably piezoelectric, electrostrictive, magnetostrictive, acoustooptic or thermo(piro) acoustic biosensors or a combination thereof, more preferably piezoelectric biosensors. In a preferred embodiment acoustic sensors of the transducer section further comprise a bioactive surface or coating which promotes specific blood-sensor interactions. Also preferred is that the acoustic blood analyzer further comprise a blood sampling means to obtain a blood sample, a fluidic section to deliver and distribute a blood sample to the acoustic sensor or sensors; an electronic section means which excites the sensor or sensors and detects changes in the operational parameters of the transducer section; and a packaging section or housing which provides mechanical and functional integrity to the transducer, fluidic and electronic section means of the analyzer as well as an interface for the analyzer with analytical laboratory systems and computer based data processing, storage and display systems.

Another object of the present invention is to provide a method for measuring blood properties including, but in no way limited to, coagulation and platelet function in a blood sample of a subject which comprises analyzing the blood sample in this acoustic blood analyzer. Qualitative as well as quantitative blood properties can be measured with the acoustic blood analyzer of the present invention. Further, use of the acoustic blood analyzer allows for relationships between the acoustic sensor electrical parameters and blood properties and their time characteristics to be identified.

Another object of the present invention is to provide a method for identifying, diagnosing and monitoring subjects at high risk for blood clots and excessive bleeding which comprises obtaining a blood sample from a subject and analyzing the blood sample in this acoustic blood analyzer. For purposes of monitoring subjects, sampling and analysis may be performed on a periodic basis depending upon the condition and the severity of the condition in the subject.

Yet another object of the present invention is to provide a method of using different vibrational modes of acoustic sensors including, but not limited to shear, torsional, and compressional modes and combinations thereof to characterize blood properties.

BRIEF DESCRIPTION OF THE FIGURES

FIG. 1A shows a shear wave sensor schematic.

FIG. 1B shows the change in attenuation ($\Delta\alpha$) during platelet adhesion (1-5 minutes) and clotting (5-25 minutes for "Clot" trace).

FIG. 1C shows the dynamics of attenuation change are delayed when clotting is prolonged.

FIG. 1D is a linegraph wherein showing the $\Delta\alpha$ vs. time slope to be zero when time is equal to clotting time (time/clotting time=1).

FIG. 3A shows a sensor operating at the fundamental frequency. FIG. 3B shows a sensor operating at the fundamental frequency and higher harmonics.

FIGS. 5A and 5B provide a schematic model of a piezoelectric sensor with two acoustic ports and one electric port (FIG. 5A), and its electric equivalent circuit representation (FIG. 5B).

DETAILED DESCRIPTION OF THE INVENTION

Figure 1B:
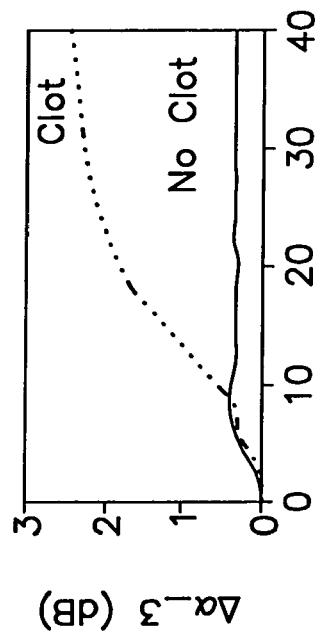
FIGS. 1A through 1D provide data from the $3^{rd}$ harmonic of a 5 MHz sensor, penetration depth approximately 150 nm.

Clinical hemostasis tests are crucial to millions of patients, who are medicated with anticoagulants and antiplatelet agents. Approximately 12 million patients who undergo surgical procedures require intraoperative or postoperative anticoagulation to reduce risks of thrombosis or stroke. Another 1.5 million patients with atrial fibrillation or prosthetic heart valves take oral anticoagulants to prevent thrombosis and stroke. While these drugs are beneficial, antithrombotic agents can also cause excessive bleeding (Levine, M. N. and J. Hirsch (1992). Hemorrhagic Complications of Long-Term Antithrombotic Treatment. *Thrombosis in Cardiovascular Disorders*. V. Fuster and M. Verstraete. Philadelphia, Saunders: 515-522), and tests of clotting time are required to determine proper dosing. Most of these tests are performed in a clinical lab, rather than at the point of care or at a patient's home ("self-test"). Patients undergoing cardiopulmonary bypass or receiving artificial blood pump implants are especially difficult to manage with traditional clotting tests (Gravlee et al. Ann Thorac Surg 1994 58(1): 216-21). The ideal hemostasis assay for such patients, the Thromboelastograph (TEG) (Shore-Lesserson et al. Anesth Analg 1999 88(2): 312-9) measures time and clot mechanical stiffness. However, TEG is difficult to use and not suitable for self-testing. Platelet function assays, that serve to differentiate platelet related bleeding problems from coagulation defects, are also costly and require specialized technician training.

The present invention provides an acousto-mechanical blood analyzer, also referred to herein as an acoustic blood analyzer or ABA, for near patient/self testing which provides accurate and timely platelet-function testing as well as analysis of the coagulation status of blood and other blood properties.

By the term "blood property" or "blood properties" as used herein it is meant to include physical, biological and/or biochemical characteristics of a blood sample. Examples include, but are in no way limited to, density, elasticity, viscosity, clot stiffness, platelet concentration, platelet activation, platelet receptor activities, GPIIb/IIIa function, GPIb function, GPIa/IIa function, blood hemostatic factor concentration, bleeding time, activated clotting time, activated partial thromboplastin time, prothrombin time, thrombin time, Fibrinogen, factor VIII deficiency, von Willebrand factor, tissue factor, specific drug concentration, or therapeutic effects of anticoagulation and antiplatelet or thrombin inhibitor drug activities. Further, by blood properties it is meant to be inclusive of characteristics which can be determined by measuring interactions of native or intrinsic components of a blood sample such as, but not limited to cells, proteins, DNAs, or enzymes in the blood or derived from the blood, as well as interactions of extrinsic or foreign components such as, but not limited to, drugs, viruses or bacteria in the blood or derived from the blood.

In simplest form, the acoustic blood analyzer comprises a transducer section of one or more acoustic sensors, preferably piezoelectric, electrostrictive, magnetostrictive, acoustooptic or thermo(piro) acoustic biosensors or a combination thereof.

Of these acoustic sensors useful in the present invention, electrostrictive, acoustooptic, and piezoelectric wave transducer modalities have emerged as some of the more promising biosensor technologies. Biosensor development is in large part dependent upon technologies primarily developed for other (e.g. industrial, aerospace, military) purposes. Silicon-based microfabrication (IC) and micromechanical (MEMS) techniques have been successfully applied in fabrication of wide range of miniature electrochemical biosensors. Similarly, progress in optically-based biosensors has its roots in fiber optics and devices designed for fiberoptic communication. In particular, piezoelectric biosensors are the benefactors of decades-long growth in RF telecommunication technologies. Other types of biosensors based on calorimetric or thermo(piro) acoustic, and magnetic magnetostrictive, techniques, among others, have benefited immensely from modern IC and MEMS research and development. Among all these innovative technologies, piezoelectric techniques offer the broadest range of sensing mechanisms, with low cost and high reliability and thus are preferred at this time for use in the present invention.

Figure 3:
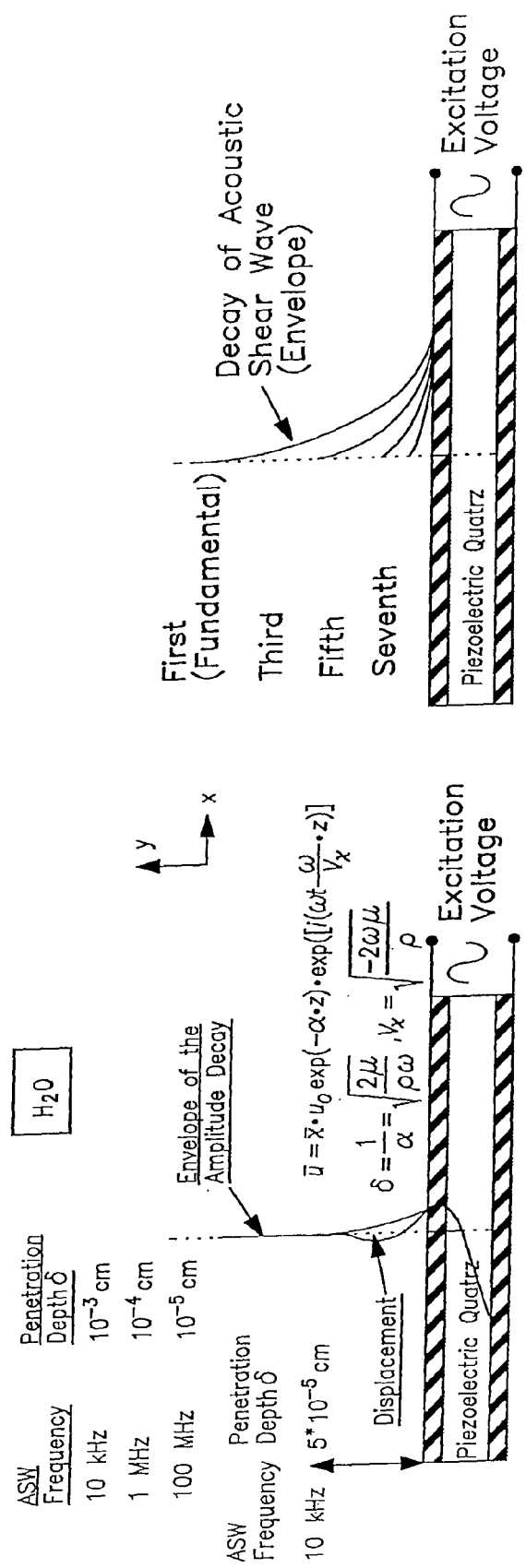
FIGS. 3A and 3B show governing equations and a deformation wave diagram of a TSM transducer exposed on one side to water loading.

In general, however, these acousto-mechanical sensors function by utilizing different types of acoustic waves to "interrogate" the entity being measured, i.e., the measurand. By the term "interrogate" or "interrogates" it is meant that the acoustic sensor generates waves that penetrate the blood sample over some controlled penetration distance or depth into the sample, as measured from the sensor-sample interface (as illustrated in FIGS. 1A and 3). The physical properties of the interrogated sample residing within the wave penetration distance will isolate specific blood sample features and give rise to characteristic signatures as detected by the ABA sensor. By exciting the sensor over a broad range of frequencies, ranging from a single KHz to several GHz, the sensor interrogates the sample over a range of distances from nanometers to centimeters from a surface of the acoustic sensor thus providing multiple measurements for a single blood sample. The acoustic waves can be generated and received by a variety of means, including piezoelectric, magnetostrictive, magnetostrictive, acoustooptic and thermo (piro) acoustic (Lec R. M., and Lewin P. A., Proceedings of 20$^{th}$ Annual IEEE Engineering in Medicine and Biology Society, 1998.20(6): p 2785-2790) techniques as well as electrostrictive techniques. Currently, from an engineering point of view, piezoelectric transducer technology offers the most efficient, inexpensive and integrated-circuit (IC) compatible way of generating of acoustic waves. Further, there are many available materials for manufacturing piezoelectric transducers including crystals, composites and hybrid structures, which provide a wide range of possible sensing material design options.

Piezoelectric transducers deliver mechanical forces to a biological medium usually in the form of progressive or standing acoustic waves. Several different types of acoustic waves can be used for the purposes of sensing biological phenomena. Knowledge of their properties is important for the selection of the optimal acoustic wave for a given biomeasurand. Acoustic waves can be considered a source of distributed force acting on a medium. The resultant deformation force acting on the medium can give rise to compression, torsional, or shear imposed forces, or a combination thereof. The type of the imposed deformation accompanying the wave is important because it determines the resultant acoustic sensing processes. For example, compressional deformation is associated with structural relaxational processes of the medium, while shear is associated with the medium viscoelastic properties, making it sensitive to different molecular processes (Matheson, A. J. "Molecular Acoustic", Wiley-Interscience, New York, 1971; Bathia, A. B "Ultrasonics Absorption", Clarendon, London (1967)). Compressional deformations are easily transmitted through any gaseous, liquid or solid media. Shear deformation, on the other hand, propagates only through solids, and penetrates only to a limited depth into liquid and gases. This latter feature is particularly advantageous, because it makes shear waves sensitive to numerous interfacial phenomena. The shear mode is therefore utilized by many acoustic wave biosensors. The wave penetration depth, which depends on the frequency of the wave and the density and viscoelastic properties of the medium, ranges from microns to nanometers. Consequently, the required sample volumes for sensing are small, and the sensitivity of the sensor is relatively high. In addition to mechanical phenomena, acoustic wave sensors can sense electrical properties of a medium. Electric field probing of a medium is either generated by acoustic wave displacement (via piezoelectric effect) or is transduced by the sensor electrode structure. Electrical parameters measurable with the acoustic sensors include, but are not limited to, transfer function, frequency, amplitude, phase and quality factor. Thus, acoustic wave sensing mechanisms are robust, capable of measuring the changes in, for example, mass/density, elastic modulus, viscosity, electrical conductivity and dielectric constant.

Acoustic waves usually are generated by an electric section means such as an AC voltage applied to the acoustic sensor or sensors attached to the surface of, for example a piezoelectric substrate, of the transducer section. These propagated waves can be classified as bulk or surface generated waves. For piezoelectric sensors, the bulk generated waves are usually excited by metalized bulk piezoelectric elements such as disks or rods, whereas the surface generated acoustic waves are excited by an interdigital system of metallic electrodes (IDT) placed on the surface of piezoelectric materials. The electrodes are used to connect the transducer with electronic circuitry for the excitation and/or reception of acoustic waves. Two of the most common configurations of piezoelectric transducers are the thin metalized disk and the interdigital transducer (IDT). The thin metalized disk generates bulk waves, which excite Thickness Shear Modes (TSM). The interdigital transducer (IDT) excites Surface Rayleigh Wave (SRW), Surface Transverse Wave (STW), Shear-Horizontal Acoustic Plate Mode (SH-APM), and Flexural Plate Wave (FPW). The STWs form a large family of waves including Shear Horizontal SAW (SH-SAW), Surface Skimming Bulk Wave (SSBW), and Love wave modes (Josse et al., On The Mass Sensitivity of Acoustic-Plate-Mode sensors, Sensors and Actuators A, vol. 53, 1996, pp. 243-248).

In the acoustic blood analyzer of the present invention, the transducer section may comprise a single acoustic sensor, two acoustic sensors, particularly for embodiments wherein measurements are compared to reference sample, or an array of acoustic sensors comprising either a single sensor type selected from piezoelectric, electrostrictive, magnetostrictive, acoustooptic or thermo(piro) acoustic sensors or a combination thereof. Arrays may also be divided into a sample area and a reference area for embodiments wherein measurements are compared to a reference. Use of an array of sensors in the transducer section improves ABA performance and allows for simultaneous detection of several blood properties. Preferably, the acoustic sensor or sensors of the transducer section is designed to generate a plurality of propagated waves consisting of either pure shear wave, combinations of shear waves, or a combination of compressional (longitudinal) and shear waves. Torsional waves can also be measured. Various geometrical configurations of the transducer section can be used including, but not limited to, plates, disks, cylinders, tubes, rods, and bars that can be made to operate individually or in combinations such as in multi-fork structures and multiplate-arrangements.

Piezoelectric nanobiosensors have broad potential to improve hemostasis testing. As shown in FIG. 1A, a shear mode sensor applies shear deformation to a blood sample, to a nano- or micro-scale depth controlled by sensor frequency. As the blood coagulates on the sensor, its mechanical properties (elasticity and viscosity) change, resulting in measurable changes in the sensor natural frequency and power attenuation. Because the sensor measures changes in clot mechanics, it has the diagnostic advantages of the TEG. When operated at high frequency, the sensor is sensitive to nanoscale cellular and subcellular processes, such as platelet adhesion (Lec, R. M. (2001). *Piezoelectric Biosensors: Recent Advances and Medical Applications*. IEEE International Frequency Control Symposium, Seattle, Wash., IEEE). These biosensors for the acoustic blood analyzer operate in shear wave mode (1 MHz-50 MHz) and combined shear/compression mode (100-500 kHz).

Piezoelectric materials such as quartz crystals, $SiO_2$, lithium niobiate ($LiNbO_3$), lithium tantalate ($LiTaO_3$), langasites and piezoelectric ceramics and electrically active polymers can be used to make acousto-mechanical transducers. These materials exhibit a rich spectrum of electro-acoustic properties such as temperature and stress compensation and strong piezoelectric properties. These materials also have outstanding mechanical properties, are chemically stable, and operate at elevated temperatures.

In a preferred embodiment, an array of high frequency sensors, preferably fabricated of AT-cut quartz crystal, and low frequency sensors, preferably made with PZT-5A piezoelectric ceramic are used. Also preferred is an embodiment, wherein the excitation section means is capable of exciting the acoustic sensors over a broad range of frequencies ranging from a single KHz to several GHz at discrete frequencies or simultaneously at all frequencies. In embodiments where the electronic means has the capability of excitation of the acoustic sensor at discrete frequencies, these discrete frequencies may comprise resonant, antiresonant, harmonic and/or anharmonic frequencies. With this frequency range the sensors are able to interrogate clot properties at depths ranging from hundreds of nanometers to tens of microns. The sensor can monitor clotting in static or flowing blood.

In static clotting assays, a blood sample is placed on the surface of the sensor. The sensor resonant frequency, attenuation, and phase is monitored using a Network Analyzer for a selected group of harmonics as a function of time. As a result the kinetics and the signatures of targeted processes can be determined. It is expected that the signatures will be unique for a given targeted blood process and will provide important biochemical information.

Figure 2:
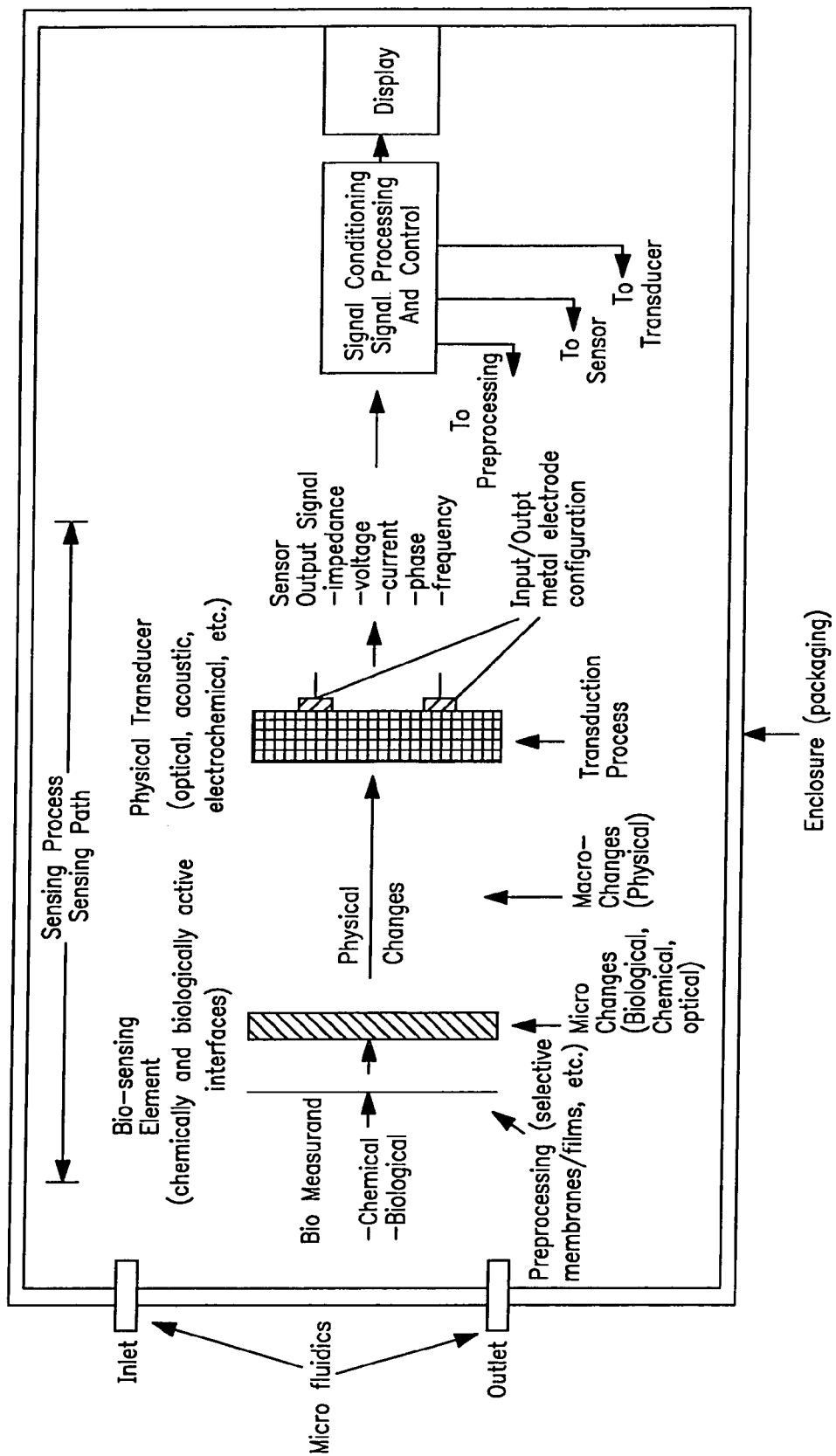
FIG. 2 is a general diagram of a preferred embodiment of an acousto-mechanical blood biosensor system of the present invention.

In a preferred embodiment, the acoustic sensor further comprises a bioactive surface or coating which promotes specific cell-sensor and blood sensor interactions. Such bioactive surfaces or coatings are selected in accordance with the blood property to be measured to promote specific interactions with native or intrinsic blood components including, but not limited to, cells, proteins, DNA, or enzymes or foreign or extrinsic blood components including but not limited to, drugs, viruses, or bacteria specific to the blood property being measured. Dedicated (bio)functionalized surfaces of acoustic sensors of the transducer section improves ABA performance and allows for detection of several blood properties A preferred design for an acousto-mechanical blood analyzer of the present invention is depicted in FIG. 2 and further comprises a fluidic section, an electronic section means and a packaging section or housing for integrating the transducer section with fluidic section and the electrical section means. Also preferred are analyzers of the present invention comprising an integrated blood sampling means.

The fluidic section of the acoustic blood analyzer is an interconnected two-dimensional or three-dimensional structure formed by the transducers that employs a microfluidic system to deliver and distribute blood samples to the sensor testing areas of the transducer section. The sensor testing areas of the transducer section are the regions close to the surface of the sensors. These areas are designed in various geometries such as cylinders or cones which are appropriate for confining blood samples at the transducer surface and maintaining its measurement integrity. The microfluidic system of the analyzer of the present invention utilizes microchannels, pumping, capillarity and/or mixing for handling blood and for creating programmable blood flow conditions. Preferably the microfluidic system or circuit utilizes programmable acoustic waves to propel the blood sample along the surface of the biosensors. Thus, the fluidic section means of the acoustic blood analyzer of the present invention has the capability of delivering blood to the acoustic transducers utilizing forces inclusive or, but not limited to, electrical, mechanical and thermal forces as well as gravitational, electrophoresis, capillary and/or magnetic forces. In addition to moving the blood sample, the fluidics section of the present invention may also mix and/or heat the blood sample to a selected temperature.

The electronic section means, also referred to as a signal processing means, of the analyzer excites the sensors of the transducer section into appropriate vibrational modes and detects changes in the operational parameters of the transducers. Vibrational modes useful for characterizing physical, biochemical and/or biological blood properties include, but are not limited to, shear, torsional, and compressional vibrational modes, as well as combinations thereof. The detected changes include variations in the transfer function, the resonant frequency, the resonant amplitude, the phase and the quality factor. Measured changes are processed, related to the targeted blood property, and displayed. Accordingly, the electronic section means comprises a system of accompanying electrical oscillatory circuits in which resonant transducer structures control their frequency, phase and the amplitude. The electronic section means used in the acoustic analyzer must be capable of excitation of the one or more acoustic sensors of the transducer section over a frequency range of a single KHz to several GHz. Excitation may be performed at discrete frequencies or simultaneously at all frequencies. When excitation is performed at discrete frequencies, these frequencies may comprise resonant, antiresonant, harmonic and/or anharmonic frequencies of the first and/or higher orders. Exemplary electronic measurement systems useful in the present invention include, but are not limited to, oscillators, phase-lock loops, vector voltmeters, sing-around circuits, network analyzers and spectrum analyzers.

The packaging section of the analyzer comprises a housing that provides mechanical and functional integrity to the transducer section, the fluidic section and the signal processing means. The packing section also provides an interface for the analyzer with analytical laboratory systems as well as computer based data processing, storage and display systems.

Some embodiments of the analyzer of the present invention may further comprise a blood sampling means integrated into the analyzer for obtaining a drop of blood from a subject. Any well-known blood collection unit can be integrated into the analyzer. Examples include, but are in no way limited to a needle, a MEMS based micro-pricking system, or a finger stick/prick collection means.

The fundamental principles of operation of the acoustic sensor or sensors used in the acoustic blood analyzer of the present invention can be inferred by following its active sensing pathway. Blood is introduced to the acoustic sensor or sensors using a blood sample collection device either separate from, or more preferably integrated in stand-alone systems of the present invention or by bringing the acoustic blood analyzer to the patient, as with other "near-patient" or indwelling biosensor probes. Accordingly, the present invention also relates to devices for measuring blood properties in the body of a subject comprising the acoustic blood analyzer of the present invention integrated into a catheter to be inserted in the body of the subject. Various configurations for stand-alone and integrated ABA systems can be used including, but not limited to, a flow-through system, a dipstick, a smart syringe or integrated in an extracorporeal blood conduit. The blood is preferably passed through a preprocessing section of the microfluidic mechanism such as a selective membrane interface, which performs an initial filtering of blood constituents. Thereafter, the blood sample is exposed to a sensing element, preferably a biologically active substance such as collagen or thromboplastin, which is selectively responsive to a measurand of interest such as platelets, blood cells, or a selected protein. When the biomeasurand interacts with the sensing element, microscopic physical, chemical, and/or biochemical changes are produced. These microscopic changes cause the macroscopic physical changes in the biosensing element, which are converted by the acousto-mechanical transducer into a measurable electric signal output. The electric signal is conditioned, processed and displayed. In particular, the processing module can be made to recognize such important sensor features as self-calibration, self-diagnostic and advanced pattern recognition analyses. All of these functional design elements can be encapsulated in the packaging unit that provides measurement integrity to the device.

The blood acousto-mechanical analyzer of the present invention can be used to measure and characterize multiple blood mechanical and acoustic properties excited at fundamental and harmonic frequencies. This allows monitoring the blood properties at different probing depths of the given blood sample ranging from distances of nanometers to centimeters from the surface of the acoustic sensors of the analyzer.

In studies with the analyzer of the present, the whole blood samples exhibited responses which were singular to the frequencies used, thus providing specific signatures corresponding to different blood interfacial processes. This feature of the acoustic blood analyzer sensing technique is unique and very important because it provides telling and interpretation-rich one-dimensional mapping of the interfacial processes and mechanical properties of the media adjacent to the sensor surface. Schematically, the cross-sectional sensing interface is depicted in FIG. 3, where a graphical representation of a distribution of shear mechanical displacement generated by a acousto-mechanical shear transducer immersed in water is given when the transducer operates at fundamental (FIG. 3a) and harmonic (FIG. 3b) frequencies. As a general rule, acoustic transducers can effectively "slice" a biological interface at different depths (FIG. 3b), hence providing important spatial information.

Figure 4:
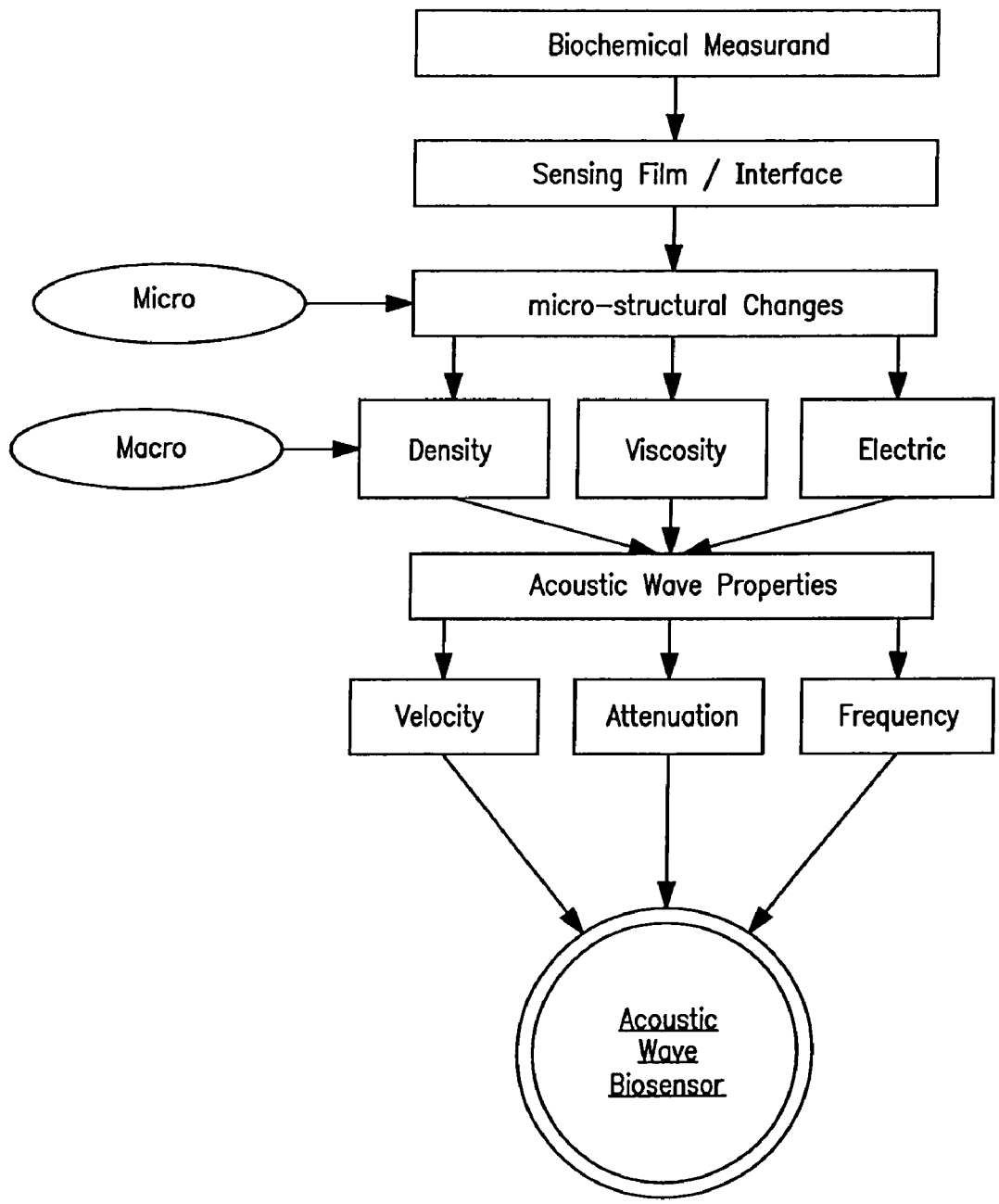
FIG. 4 provides a schematic representation of the acoustic blood analyzer sensing process.

Using the analyzer of the present invention properties including but not limited to the density, viscosity, elasticity, electric conductivity and dielectric constant of blood can be assessed by the blood-sensing element interface undergoing changes (during the measurement process), which in turn modify the acoustic field quantities of the acoustic wave transducer. Macroscale changes in elastic and visco-elastic properties of blood have been used successfully to monitor and characterize blood clotting in the thromboelastograph (TEG) and the clot rheometer. The acousto-mechanical wave transducer, which consists of an acoustic sensor, preferably a piezoelectric element with an array of metal electrodes, acts as an energy converter which transducts biomeasurands into output electric signal. For example, in the blood piezoelectric sensors a collagen thin film can be deposited as the bioactive agent on the surface of the transducer. When the target measurand, such as platelets, interact with the sensing collagen coated surface, the resultant elasticity, density and viscosity of the film can vary, modifying the acoustic parameters of the sensor and thereby leading to the changes in the output sensor signal. Schematically, the sensing sequence process is depicted in FIG. 4.

Since the boundary conditions or the topography of a sensor surface are particularly important and influence sensor response, it is preferred that the acoustic blood analyzer surface be functionalized with programmable properties in order to achieve the requested specificity and sensitivity of the sensors.

Various biofunctionalization strategies for increasing sensor specificity and sensitivity through a bioactive agent on the surface of biosensor can be used.

For example, in one embodiment the sensor is coated with an antibody specific to an unactivated or activated coagulation factor such as factors II, V, VII, VIII, IX, X, IX, or an activated coagulation enzyme complex such as tenase or prothrombinase, or to von Willebrand factor. Such coating will increase the sensor sensitivity to the target factor when the sample is interrogated at the appropriate molecular length scale.

In another embodiment, the sensor surface may coated with a specific activator of a coagulation factor, such as tissue factor, the natural extrinsic activator or coagulation factor VII (see example 5).

In another embodiment, the sensor may be coated with fibrillar collagen to increase sensor sensitivity to platelet adhesion and von Willebrand factor adsorption. In the platelet adhesion assay configuration, the blood flow shear rate at the sensor surface may be controlled by the microfluidic circuit design to preferentially measure either function of platelet GPIa/IIa at lower shear rates, or function of GPIb at high shear rates.

In another embodiment, the sensor surface may be coated with fibrinogen to increase sensitivity to platelet activation and GPIIb/IIIa function. Further, platelet activation may be stimulated by addition of agonists including but not limited to ADP, epinephrine, a stable thromboxane analog, or platelet activating factor.

In another embodiment, the sensor surface may be coated with a specific antithrombin or thrombin inhibitor such as PPACK or hirudin to increase sensitivity to thrombin generation at the sensor surface.

In another embodiment, the sensor surface may be coated with a substrate for thrombin or another coagulation cascade activated factor, which may be digested by the factor leading to a sensor attenuation decrease at the time of factor activation.

In another embodiment, the sensor may be coated with phospholipids such as, but not limited to, phosphoryl choline and phosphoryl serine to provide a substrate for coagulation complex (tenase and prothrombinase) assembly and to enhance sensor sensitivity to tenase and prothrombinase.

In yet another embodiment, the sensor is coated with an antibody capable of detecting a selected intrinsic or extrinsic component in the blood. For example, the sensor can be coated with an antibody to a cell specific antigen such as an antigen on the surface of leukemia cells.

An important feature of a piezoelectric sensor is that it can directly measure mechanical/acoustic properties of liquid medium by electrical means. In piezoelectric materials, the electro-acoustic transduction takes place within the material and is almost instantaneous. Therefore, any changes in the liquid are quickly (msec) detected by the sensor. A knowledge of the nature of this sensing process is critical for proper interpretation of the sensor response. When one applies a voltage to the sensor, the sensor creates a shear deformation/displacement at the interface. This deformation is transmitted, via the boundary conditions, to the liquid media such that a stress field is generated at the interface. The parameter that characterizes (captures) that process is the mechanical impedance of the solid-liquid interface. Effectively, the piezoelectric sensor can be modeled as a microdevice that transforms mechanical impedance into electrical impedance as schematically shown in FIG. 5A. The electro-mechanical impedance has a resonant property that can be represented in the form of an electric circuit given in FIG. 5B. The components of that circuit are functions of the piezoelectric material ($C_o$, $L_1$, $C_1$ and $R_1$) and the measured media, (L2 and R2 are related to liquid medium, and L3 describes mass deposition at the surface). The mathematical expressions are a dependent function of assumed (or measured) properties of the liquid medium. Thus, blood properties are measured by correlating an electrical property of the acoustic sensor utilizing a mathematical solution to the coupled Newton, Maxwell and blood constitutive equations, and the boundary conditions representing an actual sensing process, and whose solutions have a form of mathematical analytical and/or numerical expressions representing the acoustic sensor electrical parameters such as the transfer function, impedance, admittance, quality factor, resonant frequency and its difference, and phase. For example, Newtonian liquids media, $\omega_s L_2 = R_2 = A \cdot (\rho \eta)^{0.5}$. For viscoelastic media these expressions are more complex. In addition, mass (solid phase) accumulation at the interface can be represented as an another inertial (inductive) component, $L_3 = B \cdot (\rho_{in})$, where A and B are the sensor constants, and $\omega_s$ is the resonant frequency of the sensor.

In general, different media and processes will be represented by different structures of the electric equivalent circuit representation and by different functional relationships between mechanical parameters and the corresponding electric components. It is important to note that such a circuit representation provides a powerful tool for quantitative interpretation of interfacial phenomena. For example, considering a sensor whose resonant frequency is $\omega_{s1} = (L_1 C_1)^{-0.5}$ and whose losses are determined by $R_1$, when immersed in liquid, it can be represented by adding new circuit elements ($L_2$ and $R_2$) to the electrical side of the sensor. The resulting resonant frequency and the associated viscous losses are made manifest by the decrease in resonant frequency $\omega_{s2} [(L_1+L_2)C_1]^{-0.5}$ and the increase in equivalent resistance $R_{tot} = R_1 + R_2$. Now, if mass (e.g. a few platelets) accumulates at the interface, the frequency will change again because the total inductance increases $L_{tot} = L_1 + L_2 + L_3$; however, the "resistive" losses will remain nearly constant. Moreover, if the mass increases and the solid layer thickens (e.g. more platelets), then some viscous losses will start to emerge, and we will observe additional $R_3$ losses. If sample conditions are such that the platelets start to acquire structural stiffness, then the viscous losses will be lower, the frequency will increase, and overall losses will decrease. Importantly, observing the evolution of the sensor response characteristics as a function of time will enable the means to monitor subtle interfacial processes, providing novel insight and interpretation of coagulation biology.

Acoustic blood sensors of the present invention can be fabricated using standard photolithographic and MEMS technology. Photolithography allows fabrication of complex sensor electrode patterns, and production of multiple sensors from a single substrate. Micromachining technology (MEMS) is used for manufacturing ABA sensors operating at high fundamental frequencies above 100 MHz. The micromachining technology, which combines the photolithographic process and plasma or chemical etching techniques, enables development of complicated mechanical and electrical sensor microstructures from a single substrate. The biological sensing interface is preferably fabricated using adsorption, evaporation, spinning, soft lithography patterning and self-assembly techniques such as described by Andersson, L. I. (Journal of Chromatography B, 2000, 745:3-13) and Kane et al. (Biomaterials, 1999.20:2363-2376). In embodiments of mass scale biosensor manufacturing process steps for a biological film attachment are integrated with the piezoelectric and electronic fabrication steps.

Use of the acoustic blood analyzer enables a broad range of medical services at a patient's home using a variety of systems that employ a personal computer and web-based guided access to the Internet. One can envision a dedicated home-based analytical diagnostic system interfaced with a computer that would monitor and store medical data, spanning the lifetime of the patient. In cases of this kind, specialized application software would be able to recognize impending health-related problems and alert the user of her or his health conditions. Small and sensitive biosensors would also assist the general population and health-care providers in monitoring a variety of "environmental conditions" critical to the health and well being of a given patient population.

The acoustic blood analyzer of the present invention is particularly useful in measuring blood coagulation, specific coagulation cascades steps, including activation of plasma factors VII, IX, XI, VIII, V, X, and II (thrombin), as well platelet functions. The acoustic blood analyzer is therefore useful in identifying, diagnosing and monitoring subjects at high risk for blood clots and excessive bleeding. For purposes of monitoring subjects, sampling and analysis may be performed on a periodic basis depending upon the condition and the severity of the condition in the subject. For example, for subject receiving anti-coagulant therapy following surgery, monitoring may be performed daily or every other day.

In general, to use the analyzer a blood sample is first prepared, for example, by taking the blood sample directly from a patient and/or mixing it with a specific reagent such as a drug or a functional chemical, or group of reagents. The prepared blood sample is then delivered to the surface of the acoustic sensor or sensors of the acoustic blood analyzer. In some embodiments, a reference fluid such as air, buffer, or a control blood sample is also placed on the surface of a second acoustic sensor of the analyzer and used as a reference and/or as a standard measurement signal. Electrical changes in the characteristic fundamental and harmonic resonant frequencies, phase, amplitude, impedance, admittance or trans-impedance/admittance of the acoustic sensor or sensors in the presence of the blood sample, and when used the reference fluid, are then monitored. The resulting signal is processed to correlate the electrical parameters of the acoustic sensor, or both the acoustic and the reference sensors, with the appropriate parameters characterizing blood properties including, but not limited to coagulation, platelet functions, and other processes. Quality assurance is implemented by minimizing the influence of the ambient conditions such as temperature fluctuation, blood flow, blood background signals, etc. on the final blood testing results. Following analysis, the blood sample is disposed of in an appropriate waste container. Results of the analysis are presented in a readable form using display screen, printer, computer, etc.

The acoustic blood analyzer of the present invention is also useful in testing the blood-compatibility of natural and synthetic materials as well as the impact of drugs on blood properties. Thus, the acoustic blood analyzer of the present invention can be used in the drug discovery process of blood related medicines.

The following nonlimiting examples are provided to further illustrate the present invention.

EXAMPLES

Example 1

Blood Samples

In experiments where active platelets are required, porcine blood is obtained from a local slaughterhouse (Hatfield Pork), drawn from a carotid/jugular incision into 3.2% trisodium citrate (1 part to 9 parts blood), and used within 8 hours. Clotting is initiated by recalcification with $CaCl_2$ solution. In some assays, ADP is added to activate platelets, or kaolin is added to directly activate intrinsic coagulation. In other assays, coagulation is delayed by addition of heparin, or clot is weakened by inhibition of platelet contraction using platelet glycoprotein inhibitors or cytochlasin D. For standardized assays, blood analogs (lyophilized blood coagulation test standards) are obtained (Heamocron) and activated with celite. In some assays, fibrinolysis is stimulated using tissue-type plasminogen activator, to evaluate potential for the sensor to detect fibrinolytic tendency.

Example 2

Analysis of Blood Samples via the Acoustic Blood Analyzer

The blood acoustic analyzer was used to monitor clotting blood under a variety of conditions. Fresh porcine blood from a carotid/jugular incision was collected into 3.2% citrate (1 part to 9 parts blood) and stored at room temperature in high-density polyethylene containers. Blood was used within 8 hours in all experiments to preserve platelet function and coagulation protein concentrations. In most experiments, clotting was initiated by addition of $CaCl_2$ solution to recalcify the blood, with rapid mixing and immediate application of 200 µL to the sensor surface using a micropipette. Ten mL of the recalcified blood was kept in a 50 mL polypropylene tube, and gently inverted periodically to monitor clotting. The clotting time was defined as the time at which the blood sample resisted inversion. In this system, clotting time was on average 10 minutes for fully recalcified blood samples. In one experiment, clotting time was delayed by reducing the $CaCl_2$ concentration of recalcified blood. In a second experiment, clotting time was delayed by addition of heparin (0.25 U/mL final concentration) to the blood sample. In some cases, 5 µM ADP was added following recalcification, to activate platelets and provide procoagulant surface which accelerates coagulation.

All experiments were conducted using a 5 MHz piezoelectric shear mode sensor. The sensor was used in two configurations. In some cases, blood was monitored directly on the gold sensor surface. In other cases, the sensor was coated by bovine achilles tendon collagen type I fibers (Sigma) suspended in acetic acid, incubated on the sensor for 60 minutes, then rinsed with isotonic saline and allowed to air dry.

For the experiments to compare sensor response to different blood constituents, platelet-rich plasma was prepared by centrifugation of 50 mL of whole blood at 300 g for 10 minutes, and gently pipetting 14 mL of supernatant. Platelet-poor plasma was prepared by centrifuging 14 mL of platelet-rich plasma at 3000 g for 30 minutes, and pipetting 9.4 mL of supernatant.

Example 3

Uncoated Sensor

Figure 1D:
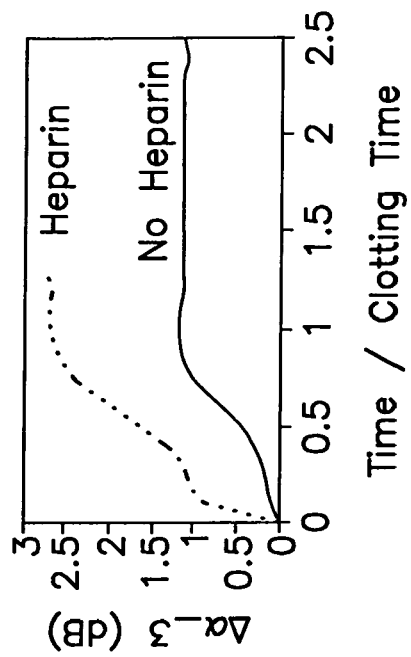
Figure 1A:
Figure 1C:
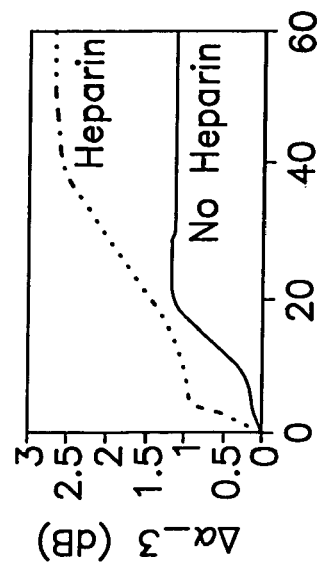

Clotting blood causes an increase in sensor attenuation and a decrease in resonant frequencies which was clearly distinguishable from citrate-anticoagulated blood, which caused a negligible change in resonant frequency, and only a small rapid increase in attenuation, as shown in FIG. 1B. The dynamics of these changes correlated with mechanical clotting time as shown in FIGS. 1C and 1D, demonstrating that the sensor is suitable for detecting clotting time. The uncoated sensor also reacted rapidly and strongly with heparin in heparinized blood samples.

Example 4

Collagen-Coated Sensor

The sensor described in example 2 was coated with bovine achilles tendon collagen type I fibers (Sigma) by adsorption from acetic acid suspension, incubated on the sensor for 60 minutes, then rinsed with isotonic saline and allowed to air dry. The collagen coating increased sensor sensitivity to early hemostatic events associated with platelet function. These early clotting events may be mediated by platelet activation, as demonstrated by the increased rate of attenuation change when ADP is added to activate platelets. The sensor response amplitude differs between whole blood, platelet-rich plasma, and platelet-poor plasma clots. This response may be indicative of specific interactions with red blood cells, or a sensitivity to clot stiffness and viscosity.

Example 5

Tissue Factor-Coated Sensor

A 10 MHz piezoelectric shear mode biosensor was coated by tissue thromboplastin (Fisher Diagnostics) by adsorption to the sensor surface from diluted solution in sodium carbonate buffer for 60 minutes, followed by rinsing with phosphate-buffered saline. 200 µl samples of platelet-poor plasma were placed on the sensor surface with buffer (control sample) or CaCl2 (recalcified sample) added and mixed. The sensor operated at the $5^{th}$ harmonic (50 MHz) was able to detect a rapid interaction between the recalcified sample and tissue-factor coated sensor, followed by a slower attenuation increase that corresponded to the bulk sample clotting time. These interactions were not observed in the control sample. The bulk clotting attenuation increase in the recalcified sample was also observed at the fundamental and $3^{rd}$ harmonic, but the early attenuation increase was greatly reduced at these frequencies.

The early interaction is attributed to activation of factor VII by the tissue factor coating on the surface, based on the calcium dependence of this activation event, the specific interaction between factor VII and tissue factor, and the increased sensitivity at higher frequencies corresponding to molecular length scales.

What is claimed is:

1. A device for analyzing blood, comprising:
   a transducer element, the transducer element including at least one of piezoelectric, electrostrictive, magnetostrictive, acousto-optic, or thermo-acoustic sensors, or a combination thereof;
   a biologically active substance in communication with the transducer element, the biologically active substance promoting interactions between the blood and the transducer element;
   a signal driver in communication with the transducer element, the signal driver applying a signal to the transducer element, and the signal driver varying a value of the signal;
   an inlet port configured to direct blood to the transducer element; and
   a signal processor in communication with the transducer element, wherein the signal processor measures a response of the blood to the signal and determines one or more characteristics of the blood as a function of the measured response.

2. The device of claim 1, wherein the transducer element includes an array of sensors.

3. The device of claim 1, wherein the biologically active substance facilitates determination of a characteristic of the blood.

4. The device of claim 1, wherein the value is at least one of the following: a frequency, an amplitude, or a phase.

5. The device of claim 4, wherein the frequency values ranges from 1 KHz to 10 GHz.

6. The device of claim 4, wherein the frequency values are provided to the transducer in at least one of the following ways: individually, sequentially, or simultaneously at the available frequencies.

7. The device of claim 4, wherein the frequency values include at least one of resonant, antiresonant, harmonic, or anharmonic frequencies of a first and higher orders.

8. The device of claim 1, wherein a depth of penetration into the blood by an effect created by the transducer element is in the range of 1 nanometer to 1 centimeter from a surface of the transducer element.

9. The device of claim 1, further comprising a catheter in communication with the transducer.

10. The device of claim 1, wherein the device is self-administered.

11. The device of claim 1, further comprising a first and second acoustic sensor, wherein the first sensor analyzes the blood, and wherein the second sensor compares the blood to a reference fluid.

12. The device of claim 1, wherein the biologically active substance is collagen, wherein the value of the signal that is varied is a frequency and the one or more characteristics including at least one of a platelet adhesion or a coagulation, and wherein a higher frequency permits detection of the platelet adhesion, and wherein a lower frequency permits detection of the coagulation.

13. The device of claim 1, wherein the biologically active substance is thromboplastin, wherein the value of the signal that is varied is a frequency and the one or more characteristics including at least one of a blood coagulation, a plasma coagulation factor concentration or a plasma coagulation factor activation, and wherein a lower frequency is applied to the transducer element to permit detection of the blood coagulation, and wherein a higher frequency is applied to the transducer element to permit detection of at least one of the plasma coagulation factor concentration or the plasma coagulation factor activation.

14. The device of claim 1, further comprising a bulk bioactive material that facilitates determination of a characteristic of the blood.

15. The device of claim 1, further comprising data storage, data processing and data transmission.

16. The device of claim 15, wherein the data storage stores at least one of the following: medical patient data, blood data, temperature, heart rate, or blood pressure.

17. The device of claim 15, wherein the data processing unit provides medical condition information to a patient.

18. The device of claim 15, wherein the data transmission unit provides wired and wireless communication between the device, a patient and a medical health center.

19. A device for analyzing blood, comprising:
a transducer element;
a biologically active substance in communication with the transducer element, the biologically active substance promoting interactions between the blood and the transducer element;
a signal driver in communication with the transducer element, the signal driver applying a signal to the transducer element, and the signal driver varying a frequency value of the signal, the frequency value ranging from 1 KHz to 10 GHz;
an inlet port configured to direct blood to the transducer element; and
a signal processor in communication with the transducer element, wherein the signal processor measures a response of the blood to the signal and determines one or more characteristics of the blood as a function of the measured response.

20. A device for analyzing blood, comprising:
a transducer element;
a biologically active substance in communication with the transducer element, the biologically active substance promoting interactions between the blood and the transducer element;
a signal driver in communication with the transducer element, the signal driver applying a signal to the transducer element, and the signal driver varying a frequency of the signal, the frequency values including at least one of resonant, antiresonant, harmonic, or anharmonic frequencies of a first and higher orders;
an inlet port configured to direct blood to the transducer element; and
a signal processor in communication with the transducer element, wherein the signal processor measures a response of the blood to the signal and determines one or more characteristics of the blood as a function of the measured response.

21. A device for analyzing blood, comprising:
a transducer element;
a biologically active substance in communication with the transducer element, the biologically active substance promoting interactions between the blood and the transducer element;
a signal driver in communication with the transducer element, the signal driver applying a signal to the transducer element, and the signal driver varying a value of the signal;
an inlet port configured to direct blood to the transducer element;
a first and a second acoustic sensor, the first sensor analyzing the blood, and the second sensor comparing the blood to a reference fluid; and
a signal processor in communication with the transducer element, wherein the signal processor measures a response of the blood to the signal and determines one or more characteristics of the blood as a function of the measured response.

22. The device of claim 21, wherein the transducer element includes at least one of: piezoelectric, electrostrictive, magnetostrictive, acousto-optic, or thermo-acoustic sensors, or a combination thereof.

23. The device of claim 21, wherein the transducer element includes an array of sensors.

24. The device of claim 21, wherein the value is at least one of the following: a frequency, an amplitude, or a phase.

25. The device of claim 24, wherein the frequency values range from 1 KHz to 10 GHz.

26. The device of claim 24, wherein the frequency values are provided to the transducer in at least one of the following ways: individually, sequentially, or simultaneously at the available frequencies.

27. The device of claim 24, wherein the frequency values include at least one of: resonant, antiresonant, harmonic, or anharmonic frequencies of a first and higher orders.

28. The device of claim 21, wherein a depth of penetration into the blood by an effect created by the transducer element is in the range of 1 nanometer to 1 centimeter from a surface of the transducer element.

29. The device of claim 21, further comprising a catheter in communication with the transducer.

30. The device of claim 21, further comprising data storage, data processing and data transmission.

31. The device of claim 30, wherein the data storage stores at least one of the following: medical patient data, blood data, temperature, heart rate, or blood pressure.

32. The device of claim 30, wherein the data processing unit provides medical condition information to a patient.

33. The device of claim 30, wherein the data transmission unit provides wired and wireless communication between the device, a patient and a medical health center.

34. The device of claim 21, wherein the value is at least one of the following: a frequency, an amplitude, or a phase, and the value is varied according to a programmable scheme.

35. A device for analyzing blood, comprising:
a transducer element;
a biologically active substance in communication with the transducer element, the biologically active substance being collagen and the collagen promoting interactions between the blood and the transducer element;
a signal driver in communication with the transducer element, the signal driver applying a signal to the transducer element, and the signal driver varying a frequency of the signal;
an inlet port configured to direct blood to the transducer element; and
a signal processor in communication with the transducer element, wherein the signal processor measures a response of the blood to the signal and determines one or more characteristics of the blood as a function of the measured response, the one or more characteristics including at least one of a platelet adhesion or a coagulation, a higher frequency permitting detection of the platelet adhesion and a lower frequency permitting detection of the coagulation.

36. A device for analyzing blood, comprising:
a transducer element;
a biologically active substance in communication with the transducer element, the biologically active substance being thromboplastin and the thromboplastin promoting interactions between the blood and the transducer element;
a signal driver in communication with the transducer element, the signal driver applying a signal to the transducer element, and the signal driver varying a frequency of the signal;
an inlet port configured to direct blood to the transducer element; and
a signal processor in communication with the transducer element, wherein the signal processor measures a response of the blood to the signal and determines one or more characteristics of the blood as a function of the measured response, the one or more characteristics including at least one of a blood coagulation, a plasma coagulation factor concentration, or a plasma coagulation factor activation, and a lower frequency being applied to the transducer element to permit detection of the blood coagulation, and a higher frequency being applied to the transducer element to permit detection of at least one of the plasma coagulation factor concentration or the plasma coagulation factor activation.

* * * * *